United States Patent [19]

Hartmann

[11] 4,349,460
[45] Sep. 14, 1982

[54] CATALYST FOR THE PREPARATION OF POLYLACTAMS

[75] Inventor: Werner Hartmann, Lindau, Fed. Rep. of Germany

[73] Assignee: Harwe AG, Schonenwerd, Switzerland

[21] Appl. No.: 246,974

[22] Filed: Mar. 24, 1981

Related U.S. Application Data

[63] Continuation of Ser. No. 114,160, Jan. 22, 1980, abandoned, which is a continuation of Ser. No. 951,910, Oct. 16, 1978, abandoned.

[30] Foreign Application Priority Data

Oct. 14, 1977 [CH] Switzerland .................. 12595/77

[51] Int. Cl.$^3$ .............................................. C08F 4/08
[52] U.S. Cl. ................................. 252/431 N; 528/312
[58] Field of Search ..................... 252/431 N; 528/312

[56] References Cited

U.S. PATENT DOCUMENTS

| | | | |
|---|---|---|---|
| 3,300,422 | 1/1967 | Bayerlein et al. | 528/312 X |
| 3,309,343 | 3/1967 | Darnell et al. | 528/312 X |
| 3,676,544 | 7/1972 | Reinking et al. | 528/312 X |
| 3,793,258 | 2/1974 | Reinking et al. | 528/312 X |
| 3,940,372 | 2/1976 | Hergenrother | 528/312 X |
| 4,115,399 | 9/1978 | Ansnos | 252/431 N X |
| 4,125,523 | 11/1978 | Bacskai | 252/431 N X |

*Primary Examiner*—Patrick Garvin
*Attorney, Agent, or Firm*—Ladas & Parry

[57] ABSTRACT

Disclosed are catalysts for the polymerization of higher lactam monomers. The catalysts comprise an essentially homogenic binary mixture of lauric-lactam and a salt of lauric-lactam.

The inventive catalyst can be stored at room temperature without making special provisions to avoid any access of air and moisture.

2 Claims, No Drawings

CATALYST FOR THE PREPARATION OF POLYLACTAMS

This application is a continuation of copending application Ser. No. 114,160 filed on Jan. 22, 1980 (now abandoned) which is in turn a continuation of application Ser. No. 951,910 filed on Oct. 16, 1978 (now abandoned).

BACKGROUND OF THE INVENTION

Several processes are known in the art for the production of polylactams by performing a polymerization of higher lactam monomers in the presence of catalysts e.g. sodium amide, sodium metal, waterfree ethanol, carbon dioxide and so on, and furthermore in the presence of an activator e.g. isocyanates or substituted lactams and so on. We e.g. refer to German Offenlegungsschrift No. 25 07 549.

If very strong basic substances are used, and especially if sodium amide is employed, then it is generally necessary to perform all working steps in an inert gas atmosphere. This is necessary because otherwise some of the above mentioned bases would react with the moisture present in the air forming undesired by-products. It has been found that a catalyst containing impurities and by-products can materially with interfere the polymerization process described in the German Offenlegungsschrift No. 25 07 549 and can also result in the deterioration of the properties of the prepared polymers of the higher lactams.

It is rather dangerous to work with larger amounts of sodium amide or similar bases because said substances are poisonous and may given rise to risk of to explosions and are furthermore extremely sensitive to traces of water. This results in the said substances being difficult to handle, especially if applied in industry.

If the substances in question are applied in industry then complicated and expensive apparatus has to be used which result in higher costs of production.

A further difficulty is that the above stated strong bases can only be difficultly dosed if the medium is not completely free of water.

A further essential point is that acids formed must be removed practically completely because otherwise the presence of acids might result in further difficulties.

SUMMARY OF THE INVENTION

One object of the invention was to avoid the above stated difficulties and to provide a catalyst for the polymerization of higher lactam monomers which can be stored easily and can be used during the polymerization reaction without any difficulties and special provisions. It has now surprisingly been found out that the aimed advantageous can be achieved by a catalyst which is an essentially homogenous binary mixture of lauric lactam and a salt thereof.

DETAILED DESCRIPTION

The object of the present invention is a catalyst for the polymerization of higher lactam monomers, which catalyst essentially comprises a homogenous binary mixture of lauric lactam and a salt of lauric lactam.

A preferred invention catalyst is one, in which the salt of the lauric lactam is the corresponding sodium salt.

A further object of the present invention is a process for the preparation of the inventive catalyst. Said process is performed by melting the monomeric lauric lactam applying an inert atmosphere and treating said melt in said inert gas atmosphere with a strong base of which the corresponding free acid is a gas, so that the lauric lactam monomer is at least partially converted into the salt form and the such liberated acid corresponding to the used base is removed from the reaction system together with the used inert gas.

According to a preferred performance of said process the strong base used is sodium amide, and the free acid corresponding to said strong base is accordingly ammonia gas, which is carried away with the inert gas used. Because of economical reasons, the preferred inert gas used for the preparation of the inventive catalyst is nitrogen.

The term "lauric lactam" as used in the present description means the lactam of the ω-amino-lauric acid, i.e. a substance having the following formula:

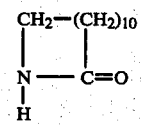

If said substance is reacted with a strong base, the hydrogen atom bonded to the nitrogen atom of the acid amide group of said lactam can be replaced by a cation, and accordingly the corresponding salt of the lauric lactam is formed.

The invention catalyst, i.e. the mixture of the lauric lactam and the salt thereof, is hardly hygroscopic and said mixture has a predetermined content of the salt. The mixture in question can be stored easily and used in the polymerization process without applying any special provisions in order to exclude air and moisture.

The inventive catalyst itself has to be produced, as outlined above, in an inert atmosphere in order to avoid a contact between the moisture of the air and the strong base used for the preparation of said catalyst. As however the apparatus for producing the catalyst is a very simple apparatus, the inert gas atmosphere can be applied therein easily and does not result in any essential additional costs.

A strong base, which can be advantageously used for the preparation of the catalyst is sodium amide. If said base is applied then the preferred material is the one sold by the Degussa Company in Germany, which has a purity of 95%. The inert gas used for the preparation of the catalyst is preferably nitrogen gas.

If sodium amide is used as strong base for the preparation of the inventive catalyst, then the reaction scheme is the following:

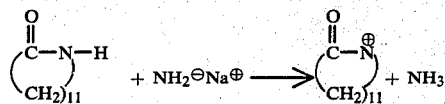

The structures of lauric lactam and the sodium salt thereof are rather similar. This can be seen from the powder-X-ray-diagrams which show similar patterns and intensities.

The new catalyst can be used for the polymerization of lactam monomers having 5-20 carbon atoms, and preferably for the polymerization of ε-caprolactam and lauric lactam respectively.

The following examples of practice of the invention are provided for illustrative purposes and provide no limitation upon the scope of the invention.

EXAMPLE 1

Preparation of a catalyst 1 kg of lauric lactam is melted at a temperature of 152° C., excluding the access of oxygen, and thereafter the melt is heated to a temperature of 167° C. Into the melt of lauric lactam there is introduced for 10 minutes waterfree nitrogen gas at a pressure of 0,1 bar.

After said treatment of the melt with the waterfree nitrogen gas there is then the nitrogen flow stopped and 40 g of pure sodium amide are added as powder or in the form of lumps. After the sodium amide had been added, the nitrogen gas is again introduced in the mixture, however now applying a lower pressure of only 0,05 bar.

During the reaction ammonia gas is evolved and the ammonia gas is carried away with the introduced nitrogen gas. The reaction is continued until the powder or the lumps of pure sodium amide are dissolved completely.

The so formed catalyst is then poured into a mold in a nitrogen atmosphere and maintained in said inert gas atmosphere until completely solidified.

EXAMPLE 2

Preparation of a catalyst 1 kg of lauric lactam is melted at a temperature of 152° C. under the strict exclusion of oxygen, and thereafter the melt is heated until a temperature of 162° C. is reached. Thereafter waterfree nitrogen gas is introduced into the melt or lauric lactam for a period of 5 minutes, applying a pressure of 0,15 bar.

Into the so pretreated molten lauric lactam there are then introduced 43,3 g of pure sodium amide which is added as powder or in the form of lumps. During the addition of the sodium amide the introduction of the nitrogen gas into the melt is interrupted. After the addition the nitrogen gas is again introduced, however now applying a reduced pressure of only 0,10 bar.

The ammonia gas formed during the reaction is removed from the mixture by the introduced nitrogen gas. This process is continued until the powder or lumps of pure sodium amide are dissolved completely.

The so produced catalyst is then poured into molds having the desired shape applying a nitrogen atmosphere and kept in the nitrogen atmosphere until the material has completely solidified.

EXAMPLE 3

Preparation of a catalyst 1 kg of lauric lactam is melted at a temperature of 152° C. excluding the access of oxygen. Then the molten material is heated until a temperature of 165° C. is reached. Into the molten lauric lactam, then waterfree nitrogen gas is introduced for 10 minutes applying a pressure of 0,1 bar.

After said treatment with the nitrogen gas the nitrogen flow is interrupted and into the molten lauric lactam there are introduced 45 g of pure sodium amide either as powder or in the form of lumps. After all the sodium amide had been added, the nitrogen gas is again introduced into the mixture, however now applying a reduced pressure of only 0,05 bar.

The now again introduced nitrogen gas carries away ammonia gas formed during the reaction. This proceeding is continued until the powder or the lumps of sodium amide are completely dissolved.

The so resulting catalyst is now poured into molds applying a nitrogen atmosphere and left under the nitrogen gas until it is completely solid.

EXAMPLE 4

Preparation of a catalyst 1 kg of lauric lactam is melted at a temperature of 152° C. excluding strictly any contact with oxygen. Thereafter the molten material is heated until to a temperature of 166° C. Into the so resulting melt of lauric lactam there is introduced for 3 minutes waterfree nitrogen gas applying a pressure of 0,2 bar.

After said pretreatment the nitrogen flow is interrupted, and into the molten lauric lactam there are added 42,4 g of pure sodium amide powder or sodium amide lumps. After the addition of the sodium amide, the nitrogen gas is again introduced into the melt, however now a reduced pressure of 0,15 bar is applied.

The introduced nitrogen gas removes the ammonia gas which is formed during the reaction. This reaction is continued until the powder or the lumps of pure sodium amide have dissolved completely.

The so formed catalyst then is poured into molds applying a nitrogen atmosphere and maintained under said atmosphere of nitrogen gas until the material has completely solidified.

The embodiment of the invention in which an exclusive property or privilege is claimed are defined as follows:

1. A catalyst for the polymerization of higher lactam monomers which consists essentially of a homogeneous binary mixture of lauric lactam and the sodium salt of lauric lactam in a ratio of 3.4 to 3.9 moles of said lactam per mole of said sodium salt.

2. A catalyst obtained by the reaction of 100 parts of weight of lauric lactam monomer with 4.0 to 4.5 parts by weight of pure sodium amide.

* * * * *